United States Patent
Bechtel et al.

(10) Patent No.: US 7,064,836 B2
(45) Date of Patent: Jun. 20, 2006

(54) BREWSTER'S ANGLE FLOW CELL FOR CAVITY RING-DOWN SPECTROSCOPY

(75) Inventors: Kate L. Bechtel, Menlo Park, CA (US); Richard N. Zare, Stanford, CA (US)

(73) Assignee: The Board of Trustees of the LeLand Stanford Junior University, Stanford, CA (US)

( * ) Notice: Subject to any disclaimer, the term of this patent is extended or adjusted under 35 U.S.C. 154(b) by 322 days.

(21) Appl. No.: 10/735,127

(22) Filed: Dec. 11, 2003

(65) Prior Publication Data

US 2004/0207852 A1 Oct. 21, 2004

Related U.S. Application Data

(60) Provisional application No. 60/464,373, filed on Apr. 21, 2003.

(51) Int. Cl.
G01N 21/00 (2006.01)

(52) U.S. Cl. ..................................... 356/440

(58) Field of Classification Search ..................... None
See application file for complete search history.

(56) References Cited

U.S. PATENT DOCUMENTS

| | | | |
|---|---|---|---|
| 5,912,740 A | 6/1999 | Zare et al. | |
| 5,943,136 A | 8/1999 | Pipino et al. | |
| 5,946,093 A | 8/1999 | DeFreez et al. | |
| 6,377,350 B1 * | 4/2002 | Paldus et al. | 356/454 |
| 6,452,680 B1 * | 9/2002 | Paldus et al. | 356/436 |
| 2003/0109055 A1 * | 6/2003 | Lehmann et al. | 436/164 |
| 2005/0094158 A1 * | 5/2005 | Paldus et al. | 356/519 |

FOREIGN PATENT DOCUMENTS

DE 43 38 972 A1 5/1995

OTHER PUBLICATIONS

Kate L. Snyder and Richard N. Zare, "Cavity Ring-Down Spectroscopy as a Detector for Liquid Chromatography", Analytical Chemistry, Jul. 1, 2003, v. 75, No. 13, pp. 3086-3091.

* cited by examiner

*Primary Examiner*—Gregory J. Toatley, Jr.
*Assistant Examiner*—Ali Allawi
(74) *Attorney, Agent, or Firm*—Patent Law Group LLP; Carmen C. Cook

(57) ABSTRACT

A container to be positioned in a ring-down optical cavity for containing a sample includes an outer surface having opposing first and second outer faces and an inner surface forming a void for containing the sample and having opposing first and second inner faces. The container may include a first portion forming the first outer face having a second index of refraction and a second portion forming the second outer face having a third index of refraction. The container may be placed in an optical cavity including a medium. The first and second outer faces of the outer surface and the first and second inner faces of the inner surface are oriented so that the cavity-to-container interfaces and the container-to-sample interfaces of the container transmit and receive a light beam at an incidence angle approximately equal to the Brewster's angle of the respective interface.

33 Claims, 3 Drawing Sheets

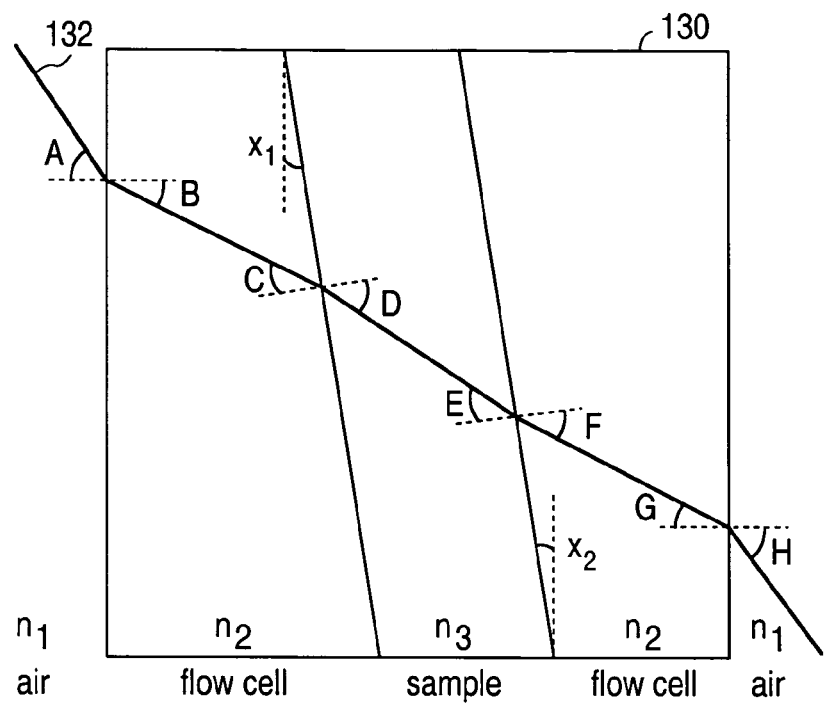
FIG. 4
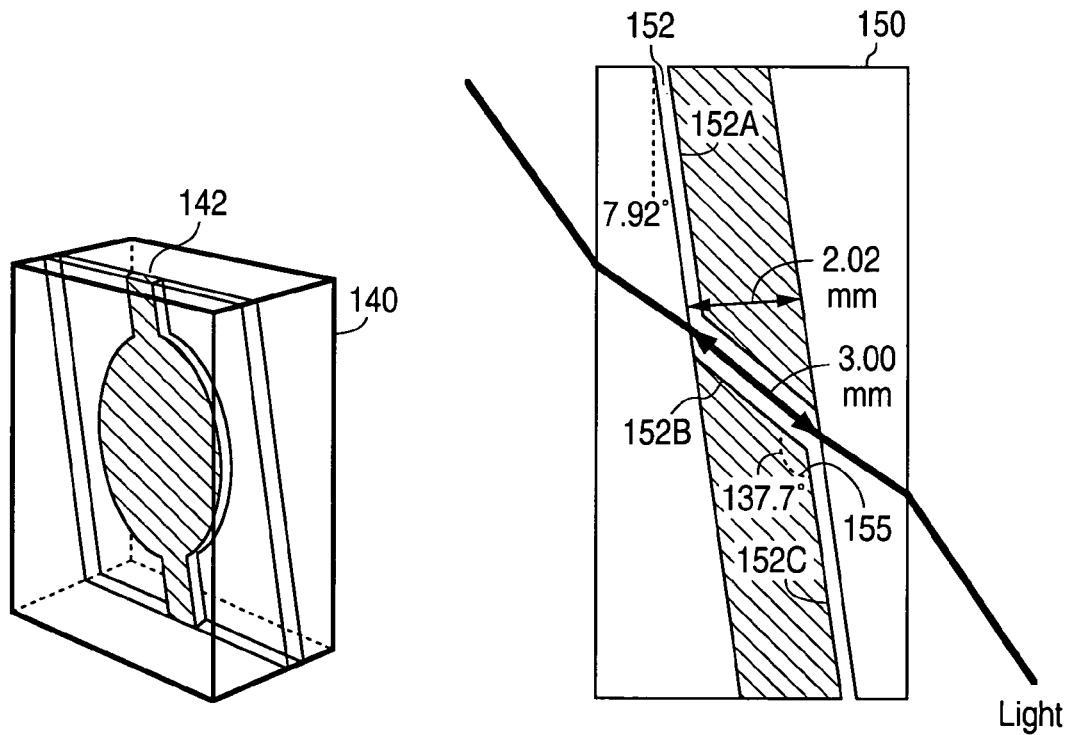
FIG. 5  FIG. 6

BREWSTER'S ANGLE FLOW CELL FOR CAVITY RING-DOWN SPECTROSCOPY

CROSS REFERENCE TO RELATED APPLICATION

This application claims the benefit of U.S. Provisional Patent Application Ser. No. 60/464,373, filed Apr. 21, 2003, entitled "Brewster Angle Cell For Cavity Ring-Down Spectroscopy Of Condensed Phase Materials," of Kate L. Snyder and Richard N. Zare, the same inventors hereof, which application is incorporated herein by reference in its entirety.

STATEMENT OF GOVERNMENT SPONSORED RESEARCH

The present invention was made with support from the Office of Naval Research under grant N00014-00-1-0364. The U.S. Government has certain rights in the invention.

FIELD OF THE INVENTION

The invention relates to an apparatus for use in spectroscopic analysis of samples with an index of refraction different than the cavity medium and, in particular, to a Brewster's angle flow cell for cavity ring-down spectroscopy of liquid, gaseous or non-rigid solid samples.

DESCRIPTION OF THE RELATED ART

High performance liquid chromatography (HPLC) is the analytical method of choice for separation, purification, and detection in numerous areas of research and industry. Of the many detection methods for liquid chromatography, the most often employed is UV-Vis absorption because it is nearly universal and is reasonably sensitive (such as on the order of $5 \times 10^{-8}$ g/mL). A fundamental limitation of traditional UV-Vis absorption detectors is the fact that a small difference between two relatively large signals is being measured. As a result, the sensitivity of absorption detectors is largely dependent on the ability to measure $I_o$ and I well enough to obtain a small $\Delta I/I$ value (currently on the order of $5 \times 10^{-5}$). Other factors influencing sensitivity are sample pathlength and the photon flux through the system. For a shot-noise-limited detector, the signal-to-noise ratio will increase as the square root of the incident light intensity. Intense light sources, such as lasers, would be desirable to increase the number of photons striking the detector, but lasers tend to suffer from intensity fluctuations, reducing their advantage. Thus, commercial absorption detectors use stable lamps (deuterium, xenon, and/or tungsten) as the light source instead of lasers. Additionally, matched photodiodes are used in some instruments to compensate for the small power fluctuations of the lamp by ratioing the outputs of the reference beam and the sample beam for each measurement. This detection scheme allows for the small $\Delta I/I$ value obtained by commercial instruments.

Insensitivity to light intensity fluctuations is an attribute of cavity ring-down spectroscopy (CRDS), a relatively new approach to absorption measurements. FIG. 1 is a schematic diagram of a simple pulsed CRDS experiment. Referring to FIG. 1, CRDS in its simplest form consists of a pulsed laser as the light source, an optical cavity formed by two highly reflective mirrors facing one another, and a detector. A laser pulse enters the cavity through the back of the first mirror and bounces back and forth inside the cavity, leaking out a small amount at each bounce. Depending on its time resolution, the detector can either resolve each individual pulse exiting the cavity or the envelope of its exponential decay, as illustrated in FIG. 1.

The rate constant for the exponential decay of light intensity depends upon all losses of light within the optical cavity. These losses include fixed losses from the optics (such as the mirrors and objects placed inside the cavity), and losses caused by absorption and scattering of the analyte and the solvent. The time constant, $\tau$, of the exponential decay of light intensity is related to the concentration of the absorbing medium by:

$$\tau = \frac{t_{rt}}{2[\delta_m + \delta_c + \alpha l]}. \qquad \text{Eq. (1)}$$

where $t_{rt}$ is the round-trip time for the light in the cavity, given by $2L/c$, where L is the cavity length and c is the speed of light, $\delta_m$ includes all mirror losses (typically approximated as $1-R$, where R is the mirror reflectivity), $\delta_c$ includes all other cavity losses not including absorption by the analyte of interest, and $\alpha l$ is the Beer's law absorption of the analyte of interest, where $\alpha$ is the per-pass absorption coefficient of the analyte and l is the sample pathlength.

The absorption coefficient $\alpha$ is related to its log base ten analog by the expression $\alpha = 2.303 \epsilon C$, in which $\epsilon$ is the molar extinction coefficient, C is the concentration and 2.303 is a constant to convert from natural log to log base ten. The absorption coefficient is determined from the ring-down time constants with and without the absorber present:

$$\alpha = \frac{t_{rt}}{2l}\left(\frac{\tau_o - \tau}{\tau_o \tau}\right) \qquad \text{Eq. (2)}$$

where $\tau$ is the ring-down time constant with the absorber present and $\tau_0$ is the ring-down time constant with only the solvent present. CRDS is insensitive to intensity fluctuations because the absorption coefficient is determined by measuring the rates of decay of the light exiting the cavity, which is not dependent on the initial light intensity (provided that the intensity is within the linear range of the detector). CRDS also has a gain in sensitivity resulting from its multi-pass nature.

The minimum detectable absorption coefficient per pass is determined by:

$$\alpha_{min} = \sqrt{2}\,\frac{L(\sigma_\tau/\overline{\tau}_o)}{lc\overline{\tau}_o} \qquad \text{Eq. (3)}$$

where $\sigma_\tau$ is the standard deviation of the mean value of the ring-down time, $\overline{\tau}_0$, without the analyte present. In the shot noise limit, $\sigma_\tau/\overline{\tau}_0$ is determined by the reciprocal of the square root of the number of photons incident on the detector. If shot noise is not the limiting factor, then to minimize $\sigma_\tau/\overline{\tau}_0$ and to maximize $\overline{\tau}_0$, the optical losses within the cavity should be reduced as much as possible. In gas-phase CRDS, where the analyte index of refraction is the same as the cavity medium, this task is typically not a problem as the only optical losses are from the cavity mirrors. Up to the point that low light throughput does not decrease the signal-to-noise (S/N) ratio by elevating the shot noise, the mirror reflectivities can be increased to achieve a lower detection limit.

In the solid and liquid phases, however, the sample must be placed within the optical cavity without it or its container introducing significant losses into the system. In the solid phase, this task has been achieved by depositing a thin film directly onto the mirror surface, by placing a rigid sample in the cavity, either perpendicular to the beam such that embedded cavities are formed or at Brewster's angle, or by evanescent wave CRDS. In evanescent wave CRDS, the sample of interest is contained on the back of a prism placed inside a ring-down cavity where the sample makes contact with the evanescent wave formed at the total-internal-reflection (TIR) surface of the prism. This technique has been applied to liquids in the study of the silica-water interface. While excellent for examining surface properties, evanescent wave CRDS is not useful for measuring the absorption properties of the bulk solution.

The application of CRDS to the measurement of the bulk absorption of liquids presents a special challenge. For instance, inserting a standard UV-Vis cuvette inside a ring-down cavity would introduce a 4% reflection loss at each surface of the cuvette, resulting in a ring-down lifetime that is too short to measure well. Various solutions to measuring bulk absorption of liquids using CRDS have been proposed. One method for performing liquid CRDS involves filling the entire ring-down cavity with the liquid of interest, allowing the liquid to come into contact with the mirrors. This approach has been applied to kinetic studies using volumes on the order of milliliters. This method is not suitable for measuring smaller volumes of liquid owing to the short ring-down lifetimes resulting from the necessarily close mirror separation.

Another method for performing liquid CRDS involves inserting a standard UV-Vis cuvette into a ring-down cavity at Brewster's angle to try to minimize the reflection losses at the interfaces of the cuvette. An example of this technique is described in U.S. Pat. No. 6,452,680 to Paldus et al. This technique is rather limited because the refractive index of the liquid sample must be close to that of the fused silica cuvette (n=1.46), which for most liquids of interest is not very common. For example, liquids that are often used as solvents for the study of many analytes are methanol and water and these liquids generally have a refractive index of approximately 1.33. Thus, even when the container is inserted into the cavity such that the cavity to container interface is at Brewster's angle, the transmitted light incident upon the container/sample interface is not necessarily at the Brewster's angle for that interface. This results in optical losses that significantly limit the ring-down time constant.

Also, the scattering and absorption loss of the large amount of solvent used in the above methods contributed to very small ring-down lifetimes. For all of these techniques, the ring-down time constant ranged from 100 to 400 ns, where detector and electronic noise prevail, and none have been applied as a detector for analytical separations.

SUMMARY OF THE INVENTION

According to one embodiment of the present invention, a container to be positioned in a ring-down optical cavity for containing a sample having a first index of refraction is described. The container can be used to facilitate measurement of light absorption in the sample. The container includes an outer surface having opposing first and second outer faces that are oriented to receive and transmit a light beam. The container includes a first portion forming the first outer face having a second index of refraction and a second portion forming the second outer face having a third index of refraction. The container further includes an inner surface forming a void for containing the sample. The inner surface has opposing first and second inner faces that are oriented to receive and transmit the light beam. The first and second outer faces of the container form first and second cavity/container interfaces and the first and second inner faces of the container form first and second container/sample interfaces.

The first and second outer faces of the outer surface of the container are to be oriented in the optical cavity such that the first and second cavity/container interfaces transmit and receive the light beam at an incidence angle approximately equal to the Brewster's angle of the respective first and second cavity/container interfaces. Furthermore, the first and second inner faces of the inner surface are oriented at first and second angles, respectively, with respect to the first and second outer faces of the outer surface such that the first and second container/sample interfaces transmit and receive the light beam at an incidence angle approximately equal to the Brewster's angle of the respective first and second container/sample interfaces.

According to another aspect of the present invention, an apparatus for measuring light absorption in a sample having a first index of refraction includes a ring-down optical cavity and a container. The ring-down optical cavity is formed by at least first and second spaced apart light beam reflectors to receive and reflect a light beam having a selected wavelength width and to establish a resonant mode for the light beam. The light beam is measured after the light beam has been reflected at least once from each reflector to determine the absorption of the light beam by the sample. The optical cavity includes a medium having a second index of refraction.

The container positioned in the optical cavity for containing the sample includes an outer surface having opposing first and second outer faces that are oriented to receive and transmit the light beam. The container includes a first portion forming the first outer face having a third index of refraction and a second portion forming the second outer face having a fourth index of refraction. The container further includes an inner surface forming a void for containing the sample. The inner surface has opposing first and second inner faces that are oriented to receive and transmit the light beam. The first and second outer faces of the container form first and second cavity/container interfaces, and the first and second inner faces of the container form first and second container/sample interfaces.

The first and second outer faces of the outer surface of the container are oriented at first and second angles, respectively, with respect to the light path of the light beam such that the light beam incident upon and exiting the first and second cavity/container interfaces is at approximately the Brewster's angle of the respective first and second cavity/container interfaces. Furthermore, the first and second inner faces of the inner surface are oriented at third and fourth angles, respectively, with respect to the first and second outer faces of the outer surface such that the light beam incident upon and exiting the first and second container/sample interfaces is at approximately the Brewster's angle of the respective first and second container/sample interfaces.

The present invention is better understood upon consideration of the detailed description below and the accompanying drawings.

BRIEF DESCRIPTION OF THE DRAWINGS

FIG. 4 is a generalized schematic of a Brewster's angle flow cell according to one embodiment of the present invention FIG. 5 is a schematic diagram of a Brewster's angle flow cell according to an alternate embodiment of the present invention.

FIG. 6 is a cross-sectional view of the side of a Brewster's angle flow cell according to an alternate embodiment of the present invention.

DETAILED DESCRIPTION OF THE PREFERRED EMBODIMENTS

In accordance with the principles of the present invention, a container to be positioned in a ring-down optical cavity for containing a sample to be analyzed includes outer faces and inner faces oriented such that light impinging on each interface of the container is at an incidence angle equal to the Brewster's angle of the interface. The container of the present invention is also referred to as a "Brewster's angle flow cell" and can be used to contain a static or a flowing liquid sample, a non-rigid solid sample or a gaseous sample. By ensuring that light incident upon and exiting each interface of the container is at the Brewster's angle of the interface, reflections of light at each interface are substantially minimized as the light travels through the container and the sample contained therein. In this manner, the container of the present invention can be placed in a ring-down optical cavity for performing cavity ring-down spectroscopy (CRDS) for liquid, gaseous, or solid samples without introducing excess loss into the system. More importantly, the use of the container of the present invention for CRDS enables a long ring-down lifetime and low noise measurement.

Furthermore, the container of the present invention enables low-volume flow-through, such as at about 10 microliter. The container of the present invention is therefore suitable for analyzing the output of a liquid chromatography separation. In general, the cell volume can be modified so that chromatography separations of varying peak volumes, such as high-performance liquid chromatography (HPLC), micro-HPLC and capillary electrophoresis (CE) can be performed.

Figure 1:
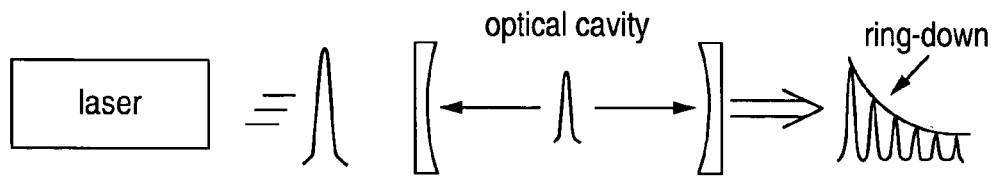
FIG. 1 is a schematic diagram of a simple pulsed CRDS experiment.
Figure 2:
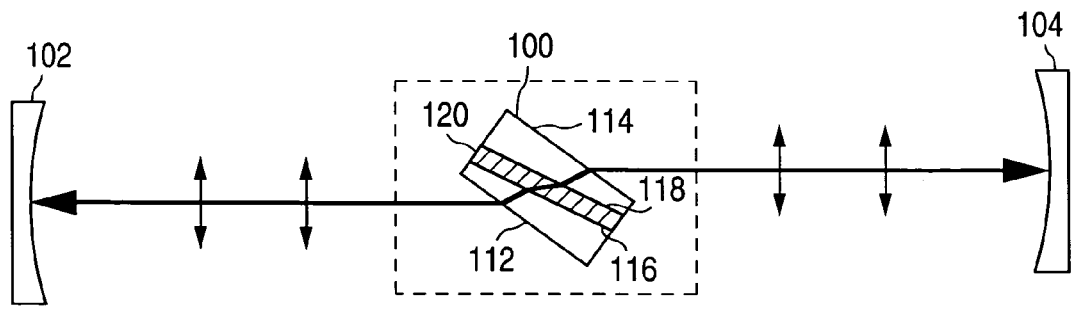
FIG. 2 is a schematic diagram of a container positioned inside a ring-down optical cavity according to one embodiment of the present invention.

FIG. 2 is a schematic diagram of a container 100 positioned inside a ring-down optical cavity according to one embodiment of the present invention. In the present description, a ring-down optical cavity refers to an optical cavity as used in CRDS that is defined by two or more high reflectivity mirrors that receive and transmit light, forming an optical resonator. A light beam of a selected wavelength, trapped by the reflectivity mirrors, bounces back and fourth between the reflecting surfaces of the mirrors.

Referring to FIG. 2, container 100, also referred to as Brewster's angle flow cell 100 or flow cell 100, is placed inside a ring-down optical cavity formed by a linear arrangement of two high reflectivity mirrors 102 and 104 separated by a given distance, such as 1 meter. In one embodiment, mirrors 102 and 105 have a reflectivity of R=0.9993 at 470 nm and are available from Los Gatos Research, Sunnyvale, Calif. In the present illustration, Brewster's angle flow cell 100 is situated at the center of the optical cavity. The optical cavity often includes a medium, such as air, inert gas or vacuum. In other embodiments, the optical cavity may include a liquid or a solid as the cavity medium. When a liquid is used as the cavity medium, the liquid can be touching the cavity mirrors. Alternately, the cavity could be formed as a monolith composed of fused silica with high reflectivity mirrors coated at the ends and a channel drilled in the monolith for containing the sample. In such case, the cavity medium is a solid of fused silica.

To perform CRDS, a source of light is provided through one of mirrors 102 and 104. The light beam has a selected wavelength $\lambda$ and a selected wavelength width. In one embodiment, the wavelength $\lambda$ is selected from a wavelength range of $0.3 \times 10^{-2}$ µm to 300 µm and the selected wavelength width is selected from a range of 0.001 $cm^{-1}$ to 1 $cm^{-1}$. In one embodiment, the light source is a Nd:YAG laser-pumped OPO oscillating at 10 Hz with a pulse duration of 10 ns. Such a laser is available from Spectra Physics MOPO, Mountain View, Calif. Furthermore, a Hamamatsu R4692 photomultiplier tube (PMT) can be used for detection of light exiting the optical cavity.

Brewster's angle flow cell 100 includes an outer surface in contact with the medium of the optical cavity and an inner surface forming a void 120 for containing the sample to be analyzed. The outer surface of flow cell 100 includes opposing first and second outer faces 112, 114 that are oriented to receive and transmit light within the optical cavity. The inner surface of flow cell 100 includes opposing first and second inner faces 116, 118 that are oriented to receive and transmit light between the container and the sample contained therein.

In the present embodiment, flow cell 100 is made of a homogeneous material and having a single index of refraction. Thus, outer faces 112 and 114 are substantially parallel and inner faces 116 and 118 are also substantially parallel. However, in other embodiments, flow cell 100 can be formed of heterogeneous materials and each outer face of the flow cell can have a different index of refraction, as will be described in more detail below. In such cases, the outer and inner faces of the flow cell are not necessarily parallel.

In Brewster's angle flow cell 100, inner faces 116 and 118 are oriented at an angle with respect to outer faces 112 and 114 in order to ensure that light impinging each surface in the optical cavity is at the correct Brewster's angle for the specific interface. In the embodiment shown in FIG. 2, the interfaces at which the incidence angle of light is equal to the Brewster's angle include the cavity medium to flow cell outer face 112, flow cell inner face 116 to sample, sample to flow cell inner face 118, and flow cell outer face 114 to the cavity medium. With the appropriate polarization of light, the reflections of light at each of the interfaces are minimized, allowing the light to pass through flow cell 100 hundreds of times, which results in a relatively long ring-down time constant. In FIG. 2, the vertical double arrows indicate the light beam is polarized parallel to the plane of incidence of the flow cell.

Brewster's angle is a function of the indices of refraction of the materials at the interface. Specifically, Brewster's angle is defined by $\tan \theta_B = n_t/n_i$, where $\theta_B$ is Brewster's angle from the normal, $n_t$ is the index of refraction of the medium in which light is transmitted and $n_i$ is the index of refraction of the medium in which light is incident. Brewster's angle defines the angle at which light plane-polarized parallel to the plane of incidence has theoretically no reflection loss. Because of the imperfect nature of most surfaces, a zero percent reflection loss is typically not realized. Nonetheless, when the interfaces are oriented at Brewster's angle, losses are sufficiently reduced to obtain a ring-down lifetime that is readily measured with little error. In one embodiment, when Brewster's angle flow cell 100 contains a sample of pure water with a 300-μm optical pathlength, a ring-down lifetime τ of 5 μs has been achieved in a 1-meter cavity.

Furthermore, flow cell 100 has been successfully coupled to HPLC so that analytes are detected by on-line absorption using CRDS.

In one embodiment, the Brewster's angle flow cell is constructed using UV-grade fused silica and polished to 15/3×0.063 as per DIN standard 58170, part 54 (similar to ISO 10110-7, Method 1). The flow thickness is 200 μm, but the optical pathlength is approximately 300 μm because of light passage at Brewster's angle. The illuminated volume is 0.5 μL and the total cell volume is 10 μL. The dead volume can be reduced if desired. In one embodiment, the Brewster's angle flow cell of the present invention is manufactured by Hellma Cells, Inc., Plainview, N.Y.

Figure 3:
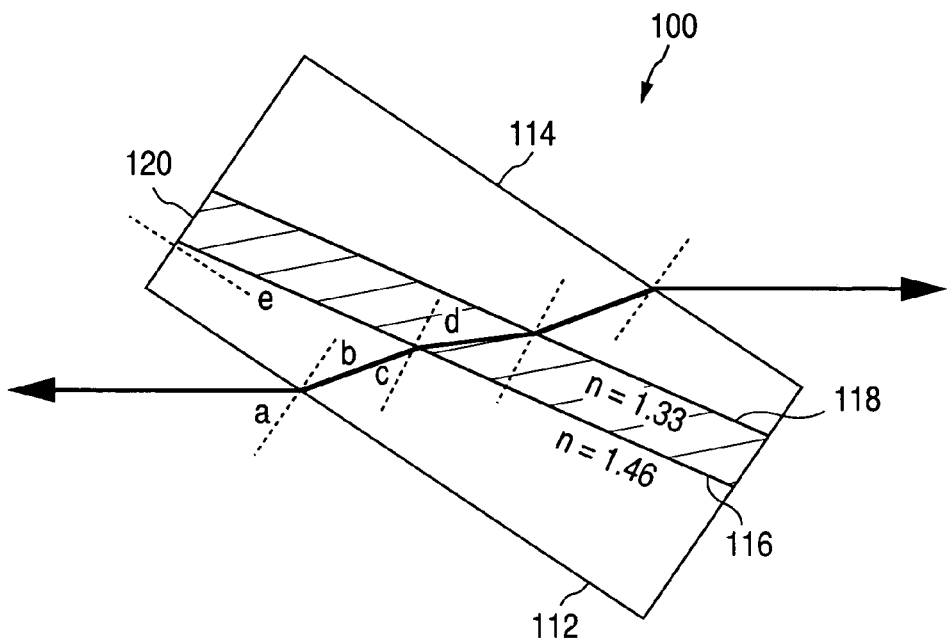
FIG. 3 is an enlarged view of the container of FIG. 2.

FIG. 3 is an enlarged view of Brewster's angle flow cell 100 of FIG. 2 and illustrates the light path as the light traverses the flow cell. By orienting the outer faces and the inner faces appropriately, the angle of incidence of light passing through each interface of flow cell 100 can be at or near the Brewster's angle for that interface. Specifically, in the present embodiment, the inner faces are tilted at a wedge angle e relative to the outer faces in order to achieve the all-interface-at-Brewster's-angle condition.

In the present description, the interface between the cavity medium and flow cell outer face 112 is referred to as the first cavity/container interface, the interface between flow cell inner face 116 to the sample is referred to as the first container/sample interface, the interface between the sample to flow cell inner face 118 is referred to as the second container/sample interface, and the interface between the flow cell outer face 114 to the cavity medium is referred to as the second cavity/container interface.

Referring to FIG. 3, the Brewster's angle for light incident upon the first cavity/container interface is denoted as a and is given by $$\tan^{-1}\left(\frac{n_c}{n_m}\right),$$

where $n_c$ is the index of refraction of the container and $n_m$ is the index of refraction of the cavity medium. The Brewster's angle for light exiting the first cavity/container interface is denoted as b and is given by $$\tan^{-1}\left(\frac{n_m}{n_c}\right).$$

The Brewster's angle for light incident upon the first container/sample interface is denoted as c and is given by $$\tan^{-1}\left(\frac{n_s}{n_c}\right),$$

where $n_s$ is the index of refraction of the sample. The Brewster's angle for light exiting the first container/sample interface is denoted as d and is given by $$\tan^{-1}\left(\frac{n_c}{n_s}\right).$$

The wedge angle e is given as a−d. The angles of the other half of the flow cell are symmetrical to the first half.

In the present embodiment, because container 100 is made of a homogeneous material, the Brewster's angles for the second container/sample interface and the second cavity/container interface are the same as the respective Brewster's angles at the first container/sample interface and the first cavity/container interface.

In one embodiment, container 100 is made of UV-grade fused silica and has a refractive index of 1.46. The sample is assumed to be water having a liquid index of refraction of 1.33. The optimal wedge angle, e, is 7.9°. With this configuration, flow cell 100 should be tilted in the optical cavity so that the angle of light incidence, a, is 55.6°. The light refracts through the cell, hitting each surface at the appropriate angle for minimum reflection. The Brewster's angles for the other interfaces are b=34.4°, c=42.3°, and d=47.7°. The angles may be altered or adjusted slightly to take into account misalignments and skew angles.

Returning to FIG. 2, to perform the simplest version of CRDS, mirrors 102 and 104 should be linear with respect to the optic axis. However, when Brewster's angle flow cell 100 is used in an optical cavity, the light beam is displaced by passage through the flow cell. In one embodiment, the light beam is displaced a few millimeters in the transverse direction by the tilt angle of the flow cell. Thus, mirrors 102 and 104 should be in offset alignment to account for the offset in the optic axis of the light beam. For example, in one embodiment, one of the mirrors, such as mirror 104, is placed on a translation stage and aligned with the flow cell in place to apply the appropriate offset.

The acceptance angle for the Brewster condition inside an optical cavity is relatively broad (±0.5°) because cavity losses are negligible unless greater than the mirror losses. For this reason, small changes in refractive index, such as those caused by absorbing species or temperature changes, do not alter significantly the ring-down time constant. Additionally, the optimum angles for the flow cell are very similar for a range of indices. Thus, a wide variety of solvents and analytes can be measured using the same flow cell. For instance, a flow cell specifically designed for a liquid with n=1.33 (nominally water) can also be used for solvents ranging from methanol (n~1.33) to acetone (n~1.36) with no more than a couple hundred nanosecond difference in the ring-down lifetime constant τ. This represented a change of no more than 10% from one solvent to the other. The differing ring-down rates result from losses induced by changes in the index of refraction and the absorption of the particular solvent. Because the ring-down time is slightly different for each solvent, this system may require calibration for gradient separations.

FIG. 4 is a generalized schematic of a Brewster's angle flow cell according to one embodiment of the present invention for further illustrating the relationship between the angles of the interfaces. In FIG. 4, a line 132 denotes the light path of the light beam as it propagates inside the optical cavity through Brewster's angle flow cell 130. The optical cavity includes a medium of air in the present illustration. The light beam enters flow cell 130 at an angle of incidence A to the outer surface of the flow cell. The light beam is refracted to an angle B and propagates through the flow cell material and arrives at the inner surface at an angle of incidence C. The light beam is then refracted to an angle D and propagates through the sample. In accordance with the present invention, the outer and inner surfaces of the flow cell are not parallel, but are offset by a wedge angle $x_1=C-B$ or A-D. The light beam exits the cell in a symmetrical fashion.

The incidence angle of each interface can be calculated as follows. At the cavity-container interfaces, the angles are given by:

$$A=H=\tan^{-1}(n_2/n_1), \text{ and}$$

$$B=G=90-A=\sin^{-1}((n_1/n_2)\sin A),$$

where $n_1$ is the index of refraction of the cavity medium (air) and $n_2$ is the index of refraction of the container. At the container-sample interfaces, the angles are given as:

$$C=F=\tan^{-1}(n_3/n_2), \text{ and}$$

$$D=E=90-C=\sin^{-1}((n_2/n_3)\sin C)$$

where $n_3$ is the index of refraction of the sample. As discussed above, the ideal angles can be altered or adjusted slightly to take into account misalignments and skew angles.

An advantageous feature of the Brewster's angle flow cell of the present invention is that the flow cell can provide a flow channel for the sample so that the sample, such as a liquid, is contained in a specified volume and optical thickness. The ability to precisely specify the volume and thickness quantities is particularly useful for detecting separations. FIG. 5 is a schematic diagram of a Brewster's angle flow cell according to an alternate embodiment of the present invention. As shown in FIG. 5, a Brewster's angle flow cell 140 can be constructed to provide a flow channel having a particular volume for the interior cavity of the flow cell. In FIG. 5, Brewster's angle flow cell 140 includes inner surfaces forming a void 142 shaped to contain a specific volume of sample. In the present illustration, void 142 includes an inlet portion, an outlet portion and an enlarged center portion. The enlarged enter portion in an oval shape for containing a desired volume of sample. The shape and the dimensions of center portion can be varied to obtain the desired volume of sample. Furthermore, the thickness of the void can also vary to provide the desired optical thickness. In this manner, the Brewster's angle flow cell of the present invention can be customized for the specific application.

As mentioned above, in some applications, it may be desirable to reduce the dead volume or excess volume of sample flowing through the Brewster's angle flow cell. According to another embodiment of the present invention, a Brewster's angle flow cell includes a flow channel where the dead volume of the sample is appreciably reduced while the optical pathlength is extended. FIG. 6 is a cross-sectional view of the side of a Brewster's angle flow cell according to an alternate embodiment of the present invention. Referring to FIG. 6, a Brewster's angle flow cell includes inner surfaces forming a void 152. Void 152 includes a first portion 152A forming an inlet for the sample, a second portion 152B forming a central channel for containing the excited or analyzed volume of the sample, and a third portion 152C forming an outlet for the sample.

First portion 152A and third portion 152C are formed with smaller dimensions to accommodate a reduced volume of sample as the sample in these locations is not being excited or analyzed. The second portion 152B, however, can be provided with enlarged dimensions to obtain the desired sample volume. According, the dead volume of the sample can be appreciably reduced in flow cell 150. Furthermore, in the present embodiment, second portion 152B is tilted at the Brewster's angle of the container to sample interface. Thus, the second portion 152B lies entirely in the light path of the light beam so that the entire volume of the central channel is exposed to the light beam. In this manner, the optical pathlength of the flow cell is extended without increasing the sample volume.

In the present embodiment, the inner surfaces forming void 152 are tilted at a wedge angle of 7.9° relative to the outer surfaces of the flow cell. The inlet (first portion 152A) has a diameter of 0.25 mm while the outlet (third portion 152C) has a diameter of 0.50 mm. The central channel (second portion 152B) has a dimension of 1.5 mm by 1.5 mm and is tilted at an angle 155 of 137.7° relative to the inner surface of the flow cell.

Figure 7:
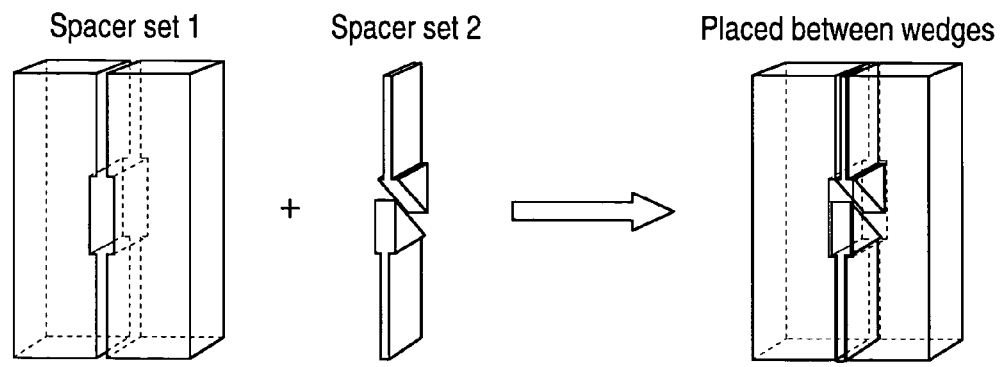
FIG. 7 illustrates a method for constructing flow cell 150 of FIG. 6 according to one embodiment of the present invention.

FIG. 7 illustrates a method for constructing flow cell 150 of FIG. 6 according to one embodiment of the present invention. Referring to FIG. 7, flow cell 150 is constructed using a first set of spacers (Spacer set 1) forming the output portions of the flow cell and a second set of spacers (Spacer set 2) forming the central channel of the flow cell. Spacer set 2 is placed between spacer set 1 to assemble flow cell 150.

Figure 8:
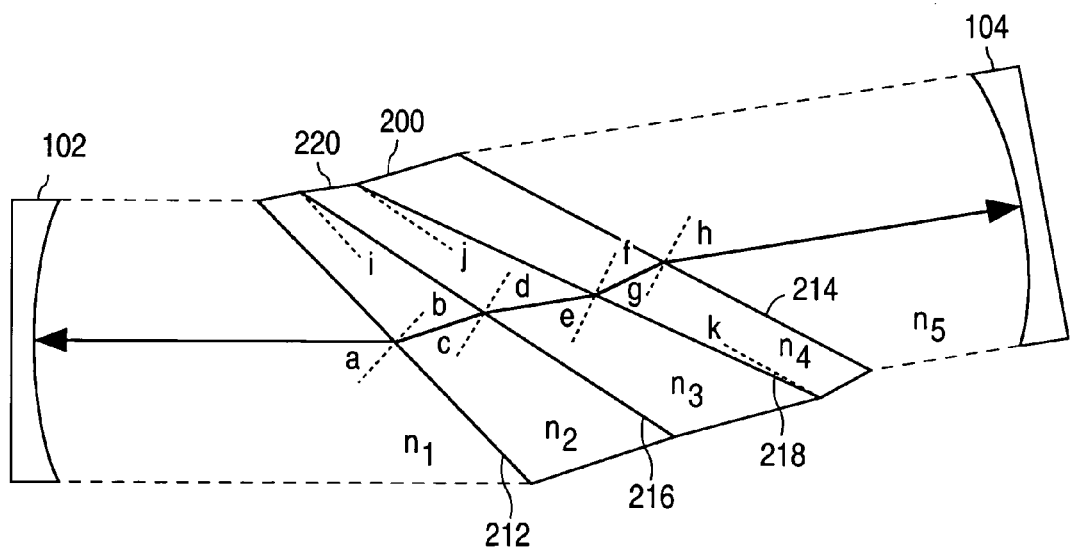
FIG. 8 is a schematic diagram of a container positioned inside a ring-down optical cavity according to an alternate embodiment of the present invention.

FIG. 8 is a schematic diagram of a container positioned inside a ring-down optical cavity according to an alternate embodiment of the present invention. Referring to FIG. 8, a container 200 or Brewster's angle flow cell 200 is positioned in an optical cavity formed by high reflectivity mirrors 102 and 104. In the present embodiment, Brewster's angle flow cell 200 is made of different materials so that a portion of the flow cell at the first outer face 212 has an index of refraction of $n_2$ and a portion of the flow cell at the second outer face 214 has an index of refraction of $n_4$. Furthermore, in the present illustration, flow cell 200 is placed in an optical cavity including different media at the opposing ends of the cavity. For instance, the optical cavity in FIG. 8 includes a first cavity medium between mirror 102 and container 200 having an index of refraction of $n_1$ and a second cavity medium between mirror 104 and container 200 having an index of refraction of $n_5$.

As thus constructed, the outer faces 212 and 214 of flow cell 200 are not parallel to each other. Furthermore, inner faces 216 and 218 of the inner surface of flow cell 200 are also not parallel to each other. Instead, inner faces 216 and 218 are oriented so that the container to sample interfaces are at the correct Brewster's angle for the respective interface.

Specifically, the Brewster's angle for light incident upon the first cavity/container interface at outer face 212 is denoted as a and is given by $$\tan^{-1}\left(\frac{n_2}{n_1}\right),$$

where $n_2$ is the index of refraction of the container at the first outer face 212 and $n_1$ is the index of refraction of the first cavity medium. The Brewster's angle for light exiting the first cavity/container interface is denoted as b and is given by $$\tan^{-1}\left(\frac{n_1}{n_2}\right).$$

The Brewster's angle for light incident upon the first container/sample interface at inner face 216 is denoted as c and is given by $$\tan^{-1}\left(\frac{n_3}{n_2}\right),$$

where $n_3$ is the index of refraction of the sample. The Brewster's angle for light exciting the first container/sample interface is denoted as d and is given by $$\tan^{-1}\left(\frac{n_2}{n_3}\right).$$

Continuing to the second container/sample interface, the Brewster's angle for light incident upon the second container/sample interface at inner face 218 is denoted as e and is given by $$\tan^{-1}\left(\frac{n_4}{n_3}\right),$$

where $n_4$ is the index of refraction of the container at the second outer face 214. The Brewster's angle for light exiting the second container/sample interface is denoted as f and is given by $$\tan^{-1}\left(\frac{n_3}{n_4}\right).$$

The Brewster's angle for light incident upon the second cavity/container interface at outer face 214 is denoted as g and is given by $$\tan^{-1}\left(\frac{n_5}{n_4}\right),$$

where $n_5$ is the index of refraction of the second cavity medium. The Brewster's angle for light exiting the second cavity/container interface is denoted as h and is given by $$\tan^{-1}\left(\frac{n_4}{n_5}\right).$$

By providing the appropriate values for wedge angles i through k, Brewster's angle flow cell 200 can be operated under the all-interface-at-Brewster's-angle condition for performing CRDS. Specifically, the angle i is given as a–d, the angle j is given as c–f, and the angle k is given as h–e.

According to another aspect of the present invention, a Brewster's angle flow cell may include multiple interfaces between a first outer face and a second outer face, where each interface transmits and receives the light beam at an incidence angle approximately equal to the Brewster's angle of the interface. In this manner, a Brewster's angle flow cell can be constructed for performing a variety of analytical experiments while maintaining a long ring-down lifetime and a high signal-to-noise ratio.

In one alternate embodiment, a Brewster's angle flow cell of the present invention includes a void for accommodating a capillary in which the sample is contained. The capillary can be inserted into the void of the flow cell to facilitate analysis of the sample. Furthermore, a sheath flow can be provided between the outer surface of the capillary and the inner surface of the flow cell. The Brewster's angle flow cell of the present invention can be constructed so that all of the interfaces within the flow cell are at a Brewster's angle of the interface, where each region of the container can involve a change of refractive index. Specifically, the interfaces include the cavity to flow cell outer surface, the flow cell inner surface to sheath flow medium, sheath flow medium to capillary, capillary to sample, sample to capillary, capillary to sheath flow medium, sheath flow medium to flow cell inner surface, and flow cell outer surface to cavity.

The Brewster's angle flow cell of the present invention has been demonstrated to work effectively in performing CRDS of liquid samples where a long ring-down time constant can be achieved with very high signal-to-noise ratio. The Brewster's angle flow cell has also been used to perform CRDS as an on-line HPLC absorption detector. Performance superior to commercially available CRDS detection systems is realized.

The Brewster's angle flow cell can be used to construct a simple pulsed CRDS system that provides a minimum detectable absorbance that is equivalent to, if not slightly better than, the best available commercial detectors. Any improvement made to the cavity ring-down system, such as operating at a higher pulse repetition rate or using a single-mode light source, will result in increased sensitivity over that currently available.

The Brewster's angle flow cell of the present invention can be modified accordingly to meet the requirement of the analytical system. For instance, the flow cell can be modified to accompany volumes suitable for micro-HPLC and possibly capillary electrophoresis (CE). In applying CRDS to nanoliter-volume systems it is necessary to focus the beam through an aperture that is generally less than 100 μm. To avoid diffraction losses and thus a reduction in the ring-down time constant, the Gaussian beam waist should be at least 4.6 times smaller than the aperture. Such a tightly focused beam in a stable resonator can be difficult to achieve. The application of CRDS to nanoliter-volume systems is an area of interest as detection limits for these low-volume techniques are comparatively quite high owing to the short pathlength of capillaries.

The above detailed descriptions are provided to illustrate specific embodiments of the present invention and are not intended to be limiting. Numerous modifications and variations within the scope of the present invention are possible. For example, in the above description, the Brewster's angle flow cell of the present invention is described as being positioned inside an optical cavity formed by two high reflectivity mirrors. The use of the Brewster's angle flow cell of the present invention in a two-mirror optical cavity arrangement is illustrative only. The Brewster's angle flow cell of the present invention can be applied to other optical cavity arrangements, such as a ring-shaped resonant cavity. A ring-shaped resonant cavity for spectroscopy is described in U.S. Pat. No. 5,912,740, which patent is incorporated herein by reference in its entirety. The present invention is defined by the appended claims.

We claim:

1. An apparatus for measuring light absorption in a sample having a first index of refraction, the apparatus comprising:
 a ring-down optical cavity formed by at least first and second spaced apart light beam reflectors to receive and reflect a light beam having a selected wavelength width and to establish a resonant mode for the light beam, the light beam being measured after the light beam has been reflected at least once from each reflector to determine the absorption of the light beam by the sample, the optical cavity comprising a medium having a second index of refraction; and
 a container positioned in the optical cavity for containing the sample, the container comprising:
  an outer surface having opposing first and second outer faces that are oriented to receive and transmit the light beam, the container including a first portion forming the first outer face having a third index of refraction and a second portion forming the second outer face having a fourth index of refraction; and
  an inner surface forming a void for containing the sample, the inner surface having opposing first and second inner faces that are oriented to receive and transmit the light beam,
  wherein the first and second outer faces of the container form first and second cavity/container interfaces, and the first and second inner faces of the container form first and second container/sample interfaces,
 wherein the first and second outer faces of the outer surface of the container are oriented at first and second angles, respectively, with respect to the light path of the light beam such that the light beam incident upon and exiting the first and second cavity/container interfaces is at approximately the Brewster's angle of the respective first and second cavity/container interfaces, and
 wherein the first and second inner faces of the inner surface are oriented at third and fourth angles, respectively, with respect to the first and second outer faces of the outer surface such that the light beam incident upon and exiting the first and second container/sample interfaces is at approximately the Brewster's angle of the respective first and second container/sample interfaces.

2. The apparatus of claim 1 wherein the medium of the optical cavity comprises one of air, an inert gas, vacuum, a liquid or a solid monolith.

3. The apparatus of claim 1, further comprising a light source for providing the light beam having a selected beam wavelength width.

4. The apparatus of claim 1, wherein the light beam has a polarization parallel to the plane of incidence of upon each interface of the container.

5. The apparatus of claim 1 wherein the third index of refraction of the first portion of the container and the fourth index of refraction of the second portion of the container are the same.

6. The apparatus of claim 5, wherein the first and second cavity/container interfaces are substantially parallel interfaces and the first and second container/sample interfaces are substantially parallel interfaces.

7. The apparatus of claim 5, wherein the container comprises UV-grade fused silica having an index of refraction of 1.46.

8. The apparatus of claim 1 wherein the sample comprises one of a liquid, gas, or solid.

9. The apparatus of claim 1, wherein the Brewster's angle of the first cavity/container interface is related to the second index of refraction and the third index of refraction and the Brewster's angle of the second cavity/container interface is related to the second index of refraction and the fourth index of refraction.

10. The apparatus of claim 1, wherein the cavity comprises a first medium between the first light beam reflector and the first outer face and a second medium between the second light beam reflector and the second outer face, the first medium having the second index of refraction and the second medium having a fifth index of refraction different from the second index of refraction.

11. The apparatus of claim 10, wherein the Brewster's angle of the first cavity/container interface is related to the second index of refraction and the third index of refraction and the Brewster's angle of the second cavity/container interface is related to the fifth index of refraction and the fourth index of refraction.

12. The apparatus of claim 1, wherein the Brewster's angle of the first container/sample interface is related to the first index of refraction and the third index of refraction and the Brewster's angle of the second container/sample interface is related to the first index of refraction and the fourth index of refraction.

13. The apparatus of claim 1, wherein the light beam has at least one selected wavelength $\lambda$.

14. The apparatus of claim 13, wherein the selected wavelength $\lambda$ is selected from a wavelength range of $0.3 \times 10^{-2}$ μm to 300 μm and the selected wavelength width is selected from a range of 0.001 cm$^{-1}$ to 1 cm$^{-1}$.

15. The apparatus of claim 1, wherein the light beam is displaced by passage through the container and the first and second spaced apart light beam reflectors are in offset alignment to account for the offset in the optic axis of the light beam.

16. The apparatus of claim 1, wherein the container further comprises a capillary positioned inside the void formed by the inner surface and a sheath flow of a second medium between an outer surface of the capillary and the inner surface of the container, the sample being contained inside the capillary, wherein the capillary is oriented in the void at a fifth angle with respect to the inner surface so that light beam incident upon and exciting an interface between the inner surface of the container and the sheath flow is at approximately the Brewster's angle of the interface, and light beam incident upon and exciting an interface between the sheath flow and the outer surface of the capillary is at approximately the Brewster's angle of the interface.

17. A container to be positioned in a ring-down optical cavity for containing a sample having a first index of refraction, the container to be used to facilitate measurement of light absorption in the sample, the container comprising:
 an outer surface having opposing first and second outer faces that are oriented to receive and transmit a light beam, the container including a first portion forming the first outer face having a second index of refraction and a second portion forming the second outer face having a third index of refraction;

an inner surface forming a void for containing the sample, the inner surface having opposing first and second inner faces that are oriented to receive and transmit the light beam;

the first and second outer faces of the container forming first and second cavity/container interfaces; and the first and second inner faces of the container forming first and second container/sample interfaces, wherein the first and second outer faces of the outer surface of the container are to be oriented in the optical cavity such that the first and second cavity/container interfaces transmit and receive the light beam at an incidence angle approximately equal to the Brewster's angle of the respective first and second cavity/container interfaces, and wherein the first and second inner faces of the inner surface are oriented at first and second angles, respectively, with respect to the first and second outer faces of the outer surface such that the first and second container/sample interfaces transmit and receive the light beam at an incidence angle approximately equal to the Brewster's angle of the respective first and second container/sample interfaces.

18. The container of claim 17, wherein the second index of refraction of the first portion of the container and the third index of refraction of the second portion of the container are the same.

19. The container of claim 18, wherein the first and second cavity/container interfaces are substantially parallel interfaces and the first and second container/sample interfaces are substantially parallel interfaces.

20. The container of claim 19, wherein the container comprises UV-grade fused silica having an index of refraction of 1.46.

21. The container of claim 17, wherein the optical cavity in which the container is to be positioned comprises a medium having a fourth index of refraction.

22. The container of claim 21, wherein the Brewster's angle of the first cavity/container interface is related to the second index of refraction and the fourth index of refraction and the Brewster's angle of the second cavity/container interface is related to the third index of refraction and the fourth index of refraction.

23. The container of claim 21, wherein the Brewster's angle of the first container/sample interface is related to the first index of refraction and the second index of refraction and the Brewster's angle of the second container/sample interface is related to the first index of refraction and the third index of refraction.

24. The container of claim 17, wherein the inner surface forming the void comprises a shaped inner surface, the shaped inner surface forming an inlet portion, an outlet portion and a central portion, the central portion having dimensions larger than the inlet portion and the outlet portion for containing a predetermined volume of sample.

25. The container of claim 17, wherein the inner surface forming the void comprises a shaped inner surface, the shaped inner surface forming an inlet portion, an outlet portion and a central portion, the central portion comprising a channel tilted at third and fourth angles relative to the first and second inner faces where the third and fourth angles are the Brewster's angle of the respective first and second container/sample interfaces.

26. The container of claim 25, wherein the central portion has dimensions larger than the inlet portion and the outlet portion for containing a predetermined volume of sample.

27. A method for measuring light absorption in a sample having a first index of refraction, the method comprising:

providing a light beam having a selected wavelength width that includes at least one selected wavelength $\lambda$;

receiving the light beam in a ring-down optical cavity formed by at least first and second spaced apart light beam reflectors to receive and reflect the light beam and to establish a resonant mode for the light beam, the optical cavity comprising a medium having a second index of refraction;

positioning a container in the optical cavity for containing the sample, the container having opposing first and second outer faces that are oriented to receive and transmit the light beam, and opposing first and second inner faces forming a void for containing the sample which inner faces are oriented to receive and transmit the light beam, the first and second outer faces forming first and second cavity/container interfaces and the first and second inner faces forming first and second container/sample interfaces, wherein positioning the container in the optical cavity comprises:

orienting the first and second outer faces of the container at first and second angles, respectively, with respect to the light path of the light beam such that the first and second cavity/container interfaces transmit and receive the light beam at an incidence angle approximately equal to the Brewster's angle of the respective first and second cavity/container interfaces; and orienting the first and second inner faces of the container at third and fourth angles, respectively, with respect to the first and second outer faces such that the first and second container/sample interfaces transmit and receive the light beam at an incidence angle approximately equal to the Brewster's angle of the respective first and second container/sample interfaces; and receiving the light beam after the light beam has been reflected at least once from each reflector to determine the absorption of the light beam by the sample.

28. The method of claim 27, wherein the third index of refraction and the fourth index of refraction are the same.

29. A method for measuring light absorption in a sample having a first refractive index, the method comprising:

providing a light beam having a selected wavelength width that includes at least one selected wavelength $\lambda$;

receiving the light beam in a ring-down optical cavity formed by at least first and second spaced apart light beam reflectors to receive and reflect the light beam and to establish a resonant mode for the light beam, the optical cavity comprising a medium having a second index of refraction;

positioning a container in the optical cavity for containing the sample, the container having first and second outer faces that are oriented to receive and transmit the light beam, and first and second inner faces forming a void for containing the sample which inner faces are oriented to receive and transmit the light beam, the first and second outer faces forming first and second cavity/container interfaces and the first and second inner faces forming first and second container/sample interfaces;

transmitting and receiving the light beam at the first cavity/container interface at an incidence angle approximately equal to the Brewster's angle of the first cavity/container interface;

transmitting and receiving the light beam at the first container/sample interface at an incidence angle approximately equal to the Brewster's angle of the first container/sample interface;

transmitting and receiving the light beam at the second container/sample interface at an incidence angle approximately equal to the Brewster's angle of the second container/sample interface;

transmitting and receiving the light beam at the second cavity/container interface at an incidence angle approximately equal to the Brewster's angle of the second cavity/container interface; and receiving the light beam after the light beam has been reflected at least once from each reflector to determine the absorption of the light beam by the sample.

30. The method of claim 29, wherein the container comprises a first portion at the first outer face having a third index of refraction and a second portion at the second outer face having a fourth index of refraction.

31. The method of claim 30, wherein the third index of refraction and the fourth index of refraction are the same.

32. The method of claim 30, wherein the Brewster's angle of the first cavity/container interface is related to the second index of refraction and the third index of refraction and the Brewster's angle of the second cavity/container interface is related to the second index of refraction and the fourth index of refraction.

33. The method of claim 30, wherein the Brewster's angle of the first container/sample interface is related to the first index of refraction and the third index of refraction and the Brewster's angle of the second container/sample interface is related to the first index of refraction and the fourth index of refraction.

* * * * *